United States Patent [19]

Sato et al.

[11] Patent Number: 5,416,212
[45] Date of Patent: May 16, 1995

[54] ANILIDE DERIVATIVES

[75] Inventors: Masakazu Sato; Masahiro Kawase; Akira Manaka; Yutaka Kawashima; Katsuo Hatayama, all of Tokyo, Japan

[73] Assignee: Taisho Pharmaceutical Co., Ltd., Japan

[21] Appl. No.: 244,998

[22] PCT Filed: Dec. 18, 1992

[86] PCT No.: PCT/JP92/01661
§ 371 Date: Jun. 20, 1994
§ 102(e) Date: Jun. 20, 1994

[87] PCT Pub. No.: WO93/13086
PCT Pub. Date: Jul. 8, 1993

[30] Foreign Application Priority Data

Dec. 25, 1991 [JP] Japan .................. 3-343576

[51] Int. Cl.$^6$ .................. C07D 295/15; C07D 401/04; C07D 403/04

[52] U.S. Cl. .................. 544/393; 544/295; 544/360; 544/400; 544/392; 544/403; 560/16; 564/214

[58] Field of Search ............... 544/295, 360, 393, 400

[56] References Cited

U.S. PATENT DOCUMENTS 3,228,949  1/1966  Risse et al. ............... 544/400
4,623,662  11/1986  De Vries ............... 514/596
4,716,175  12/1987  Hoefle et al. ............... 514/357

FOREIGN PATENT DOCUMENTS 60-41655  3/1985  Japan .
63-253060  10/1988  Japan .

*Primary Examiner*—Emily Bernhardt
*Attorney, Agent, or Firm*—Lorusso & Loud

[57] ABSTRACT

An anilide compound represented by formula (I):

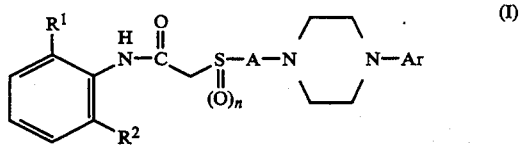

wherein $R^1$ and $R^2$, which may be the same or different, each represent an alkyl group having 1 to 4 carbon atoms; n represents 0, 1 or 2; A represents an alkylene group having 1 to 14 carbon atoms or a group represented by —CH$_2$CO—; and Ar represents a phenyl group, a phenyl group substituted with a halogen atom, a nitro group, an alkyl group having 1 to 4 carbon atoms, an alkoxy group having 1 to 4 carbon atoms, an alkanoyl group having 2 to 5 carbon atoms or a trifluoromethyl group, a benzyl group, a pyridyl group, a pyridyl group substituted with a halogen atom or a trifluoromethyl group, or a pyrimidyl group, or a salt thereof. The disclosed anilide compounds have potent ACAT inhibitory activity.

4 Claims, No Drawings

ANILIDE DERIVATIVES

TECHNICAL FIELD

This application is a 371 of PCT/JP92/01661 filed Dec. 18, 1992.

This invention relates to an anilide derivative having a piperazine ring and a salt thereof, and more particularly to an anilide derivative having a piperazine ring and a salt thereof which have acyl-CoA cholesterol acyltransferase (hereinafter abbreviated as ACAT) inhibitory activity.

BACKGROUND OF THE INVENTION

An ACAT inhibitor is believed to act on the atherosclerotic lesions to inhibit accumulation of cholesterol esters thereby inhibiting onset and progress of atherosclerosis and also act on the mucosa of the small intestine to inhibit absorption of cholesterol.

It is also considered that an ACAT inhibitor suppresses formation of cholesterol esters in the liver, which leads to reduction in blood cholesterol level (see V. A. Kosykh. et al., *Atherosclerosis*, Vol. 68, pp. 67–76 (1987)).

Among known ACAT inhibitors, the compounds disclosed in U.S. Pat. No. 4,623,662, JP-A-60-41655, and JP-A-63-253060 (the term "JP-A" as used herein means an "unexamined published Japanese patent application") are structurally similar to the anilide derivatives of the present invention but their ACAT inhibitory action is not sufficient.

An object of the present invention is to provide a compound having a potent ACAT inhibitory activity.

DISCLOSURE OF THE INVENTION

As a result of extensive investigations for accomplishment of the above object, the inventors have found that certain anilide derivatives having a piperazine ring exhibit a potent ACAT inhibitory activity and completed the present invention.

The present invention provides an anilide derivative represented by formula (I):

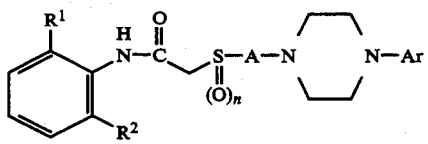

(I)

wherein $R^1$ and $R^2$, which may be the same or different, each represent an alkyl group having 1 to 4 carbon atoms; n represents 0, 1 or 2; A represents an alkylene group having 1 to 14 carbon atoms or a group represented by —CH$_2$CO—; and Ar represents a phenyl group, a phenyl group substituted with a halogen atom, a nitro group, an alkyl group having 1 to 4 carbon atoms, an alkoxy group having 1 to 4 carbon atoms, an alkanoyl group having 2 to 5 carbon atoms or a trifluoromethyl group, a benzyl group, a pyridyl group, a pyridyl group substituted with a halogen atom or a trifluoromethyl group, or a pyrimidyl group, or a salt thereof.

The details of the present invention will hereinafter be described.

The alkyl group having 1 to 4 carbon atoms is a straight- or branched-chain alkyl group. The alkylene group having 1 to 14 carbon atoms is a straight-chain alkylene group. The halogen atom is a fluorine atom, a chlorine atom, a bromine atom or an iodine atom. The alkoxy group having 1 to 4 carbon atoms is a straight- or branched-chain alkoxy group. The alkanoyl group having 2 to 5 carbon atoms is a straight- or branched-chain alkanoyl group. The salt of the compound of formula (I) includes a hydrochloride, a sulfate, an acetate, a maleate, a tartrate, a citrate, a succinate, a methanesulfonate, a p-toluenesulfonate, a malate, and a fumarate.

Of the compounds according to the present invention preferred are those in which $R^1$ and $R^2$ are each an isopropyl group; n is 0; A is an alkylene group having 1 to 14 carbon atoms; and Ar is a phenyl group. More preferred are those in which $R^1$ and $R^2$ are each an isopropyl group; n is 0; A is an alkylene group having 6 or 8 carbon atoms; and Ar is a phenyl group. The most preferred is the compound in which $R^1$ and $R^2$ are each an isopropyl group; n is 0; A is an alkylene group having 6 carbon atoms; and Ar is a phenyl group, i.e., N-(2,6-diisopropylphenyl)-2-[6-(4-phenylpiperazinyl)hexylthio]acetamide.

The compound of formula (I) can be prepared by, for example, reacting an anilide derivative represented by formula (II):

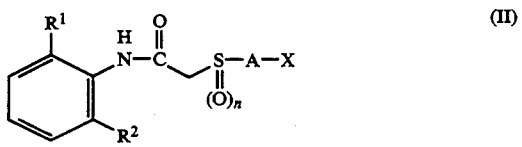

(II)

wherein $R^1$, $R^2$, n, and A are as defined above; and X represents a halogen atom, with a compound represented by formula:

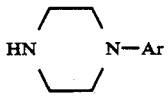

wherein Ar is as defined above, in the presence or absence of a base.

The compound of formula (II) is a novel compound, which can be synthesized from a known compound, for example, as follows.

(1) The compound of formula (II) wherein A is an alkylene group is synthesized by hydrolyzing the thioester moiety of a compound represented by formula (III):

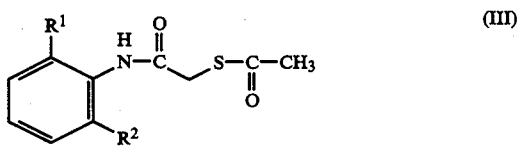

(III)

wherein $R^1$ and $R^2$ are as defined above, in the presence of a base, reacting the resulting thiol compound with a compound represented by formula:

wherein X is as defined above; Y represents a halogen atom, which may be the same with or different from X; and m represents an integer of from 1 to 14, in the presence or absence of a base, and, if necessary, oxidizing the sulfur atom of the thioether moiety of the resulting compound with an appropriate oxidizing agent.

The bases which can be used in the above reactions include alkali salts, such as potassium carbonate, sodium carbonate, sodium hydroxide, and potassium hydroxide; amines, such as triethylamine, diisopropylethylamine, and pyridine; sodium hydride, potassium hydride, sodium amide; and alkoxides, such as sodium methoxide, sodium ethoxide, and potassium t-butoxide. The sulfur atom oxidizing agent which can be used in the above reaction includes hydrogen peroxide, m-chloroperbenzoic acid, and peracetic acid. In using a solvent for the reactions, solvents inert to the reactions, such as water, alcohols, tetrahydrofuran, N,N-dimethylformamide, dimethyl sulfoxide, methylene chloride, chloroform, acetone, toluene, and benzene, may be used.

(2) The compound of formula (II) wherein A is —CH$_2$CO— is obtained by reacting an anilide derivative represented by formula:

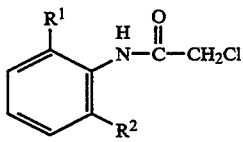

wherein R$^1$ and R$^2$ are as defined above, with a compound represented by formula:

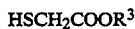

HSCH$_2$COOR$^3$ wherein R$^3$ represents a lower alkyl group, to form an ester represented by formula:

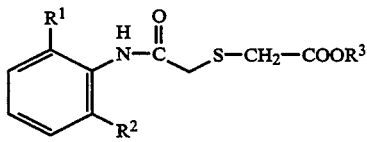

wherein R$^1$ R$^2$ and R$^3$ are as defined above, if necessary oxidizing the sulfur atom of the thioether moiety of the ester with an appropriate oxidizing agent, and further conducting hydrolysis and conversion to an acid halide according to a usual manner.

The compound of formula (I) wherein A is an alkylene group and n is 0 can also be synthesized by hydrolyzing the thioester moiety of the compound of formula (III) in the presence of a base and reacting the resulting thiol with a compound represented by formula:

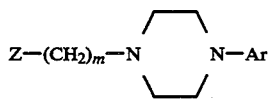

wherein Ar and m are as defined above; and Z represents a halogen atom, in the presence or absence of a base.

For use as an agent for atherosclerosis inhibition or an agent for cholesterol reduction, the compound of formula (I) is administered orally or non-orally in various dose forms, such as tablets, granules, powders, pills, capsules, injectable solutions, and the like. These preparations are prepared by using additives, such as vehicles, binders, lubricants, disintegrators, dissolving agents, and pH adjusting agents, in accordance with general formulation techniques. The dose of the compound of formula (I) usually ranges from 2 to 2000 mg per day in a single or several divided doses, while varying depending on the age of a patient, the type or conditions of the disease.

BEST MODE FOR EMBODYING THE INVENTION

The present invention will no be illustrated in greater detail with reference to Examples.

EXAMPLE 1

N-(2,6-Diisopropylphenyl)-2-[6-(4-phenylpiperazinyl)-hexylthio]acetamide (Compound 1)

(1) To a mixture of 29.3 g of N-(2,6-diisopropylphenyl)-2-(acetylthio)acetamide and 240 ml of ethanol was added dropwise 27 ml of a 30% aqueous sodium hydroxide solution at 0° C. in an argon atmosphere. After stirring for 30 minutes, 20.0 g of 1-bromo-6-chlorohexane was added thereto, followed by stirring at room temperature for 4 hours. To the reaction mixture was added 50 ml of water to yield 36.0 g of N-(2,6-diisopropylphenyl)-2-(6-chlorohexylthio)acetamide as colorless needle crystals having a melting point (m.p.) of 86.5° to 87.5° C.

The compounds listed below were synthesized in the same manner as in Example 1-(1), except for replacing 1-bromo-6-chlorohexane with the respective starting compound.

N-(2,6-Diisopropylphenyl)-2-(2-chloroethylthio)acetamide (m.p.=77.0°–80.0° C.);

N-(2,6-Diisopropylphenyl)-2-(3-chloropropylthio)acetamide (m.p.=146.0°–150.0° C.);

N-(2,6-Diisopropylphenyl)-2-(4-chlorobutylthio)acetamide (m.p.=129.5°–131.0° C.);

N-(2,6-Diisopropylphenyl)-2-(6-bromohexylthio)acetamide (m.p.=90.5°–91.5° C.);

N-(2,6-Diisopropylphenyl)-2-(8-bromooctylthio)acetamide (m.p.=58.0°–59.0° C.); and N-(2,6-Diisopropylphenyl)-2-(9-bromononylthio)acetamide (m.p.=59.0°–60.0° C.).

(2) A mixture of 7.4 g of the compound synthesized in (1) above, 3.4 g of N-phenylpiperazine, 3.2 g of diisopropylethylamine, and 50 ml of toluene was heated under reflux for 24 hours. To the reaction mixture was added 100 ml of ethyl acetate, and the mixture was washed successively with water and a saturated sodium chloride aqueous solution, and dried over magnesium sulfate. The solvent was evaporated under reduced pressure, and the residue was subjected to column chromatography using a 1:2 mixture of ethyl acetate and hexane as a developing solvent. Crystallization from hexane and recrystallization from isopropyl alcohol-water gave 3.5 g of the title compound as white powder (m.p.=85.0°–86.0° C.).

The following compounds were obtained in the same manner as in Example 1-(2), except for replacing N-phenylpiperazine with the respective starting material.

N-(2,6-Diisopropylphenyl)-2-{6-[4-(2-methoxyphenyl)-piperazinyl]hexylthio}acetamide dihydrochloride (Compound 2) (m.p.=130.0°–132.0° C.);

N-(2,6-Diisopropylphenyl)-2-{6-[4-(4methoxyphenyl)-piperazinyl]hexylthio}acetamide (Compound 3) (m.p.=98.0°–99.0° C.);

N-(2,6-Diisopropylphenyl)-2-{6-[4-(2-chlorophenyl)-piperazinyl]hexylthio}acetamide (Compound 4) (m.p.=63.0°–64.0° C.);

N-(2,6-Diisopropylphenyl)-2-{6-[4-(2pyridyl)-piperazinyl]hexylthio}acetamide (Compound 5) (m.p.=79.6°–81.0° C.);

N-(2,6-Diisopropylphenyl)-2-{6-[4-(2-pyrimidyl)-piperazinyl]hexylthio}acetamide (Compound 6) (m.p.=82.3°–83.7° C.);

N-(2,6-Diisopropylphenyl)-2-{6-[4-(3-chlorophenyl)-piperazinyl]hexylthio}acetamide (Compound 7) (m.p.=81.7°–83.7° C.);

N-(2,6-Diisopropylphenyl)-2-{6-[4-(3-methylphenyl)-piperazinyl]hexylthio}acetamide (Compound 8) (m.p.=89.9°–90.9° C.);

N-(2,6-Diisopropylphenyl)-2-{6-[4-(2-methylphenyl)-piperazinyl]hexylthio}acetamide fumarate (Compound 9) (m.p.=147.7°–150.2° C.);

N-(2,6-Diisopropylphenyl)-2-{6-[4-(3-trifluoromethylphenyl)piperazinyl]hexylthio}acetamide (Compound 10) (m.p.=64.0°–65.° C.);

N-(2,6-Diisopropylphenyl)-2-{6-[4-(4-fluorophenyl)-piperazinyl]hexylthio}acetamide (Compound 11) (m.p.=89.6°–92.0° C.);

N-(2,6-Diisopropylphenyl)-2-{6-[4-(2-nitrophenyl)-piperazinyl]hexylthio}acetamide (Compound 12) (m.p.=49.7°–52.2° C.);

N-(2,6-Diisopropylphenyl)-2-{6-[4-(4-acetophenyl)-piperazinyl]hexylthio}acetamide (Compound 13) (m.p.=108.9°–110.1° C.);

N-(2,6-Diisopropylphenyl)-2-{6-[4-(6-trifluoromethyl-2-pyridyl)piperazinyl]hexylthio}acetamide (Compound 14) (m.p.=88.1°–89.4° C.);

N-(2,6-Diisopropylphenyl)-2-{6-[4-(4-chloro-2-pyridyl)piperazinyl]hexylthio}acetamide (Compound 15) (m.p.=113.6°–114.6° C.);

N-(2,6-Diisopropylphenyl)-2-{6-[4-(4-chlorophenyl)-piperazinyl]hexylthio}acetamide (Compound 16) (m.p.=117.0°–119.2° C.);

N-(2,6-Diisopropylphenyl)-2-[2-(4-phenylpiperazinyl)ethylthio]acetamide dihydrochloride (Compound 17) (m.p.=176.0°–179.0° C.);

N-(2,6-Diisopropylphenyl)-2-[3-(4-phenylpiperazinyl)propylthio]acetamide dihydrochloride (Compound 18) (m.p.=185.5°–187.5° C.);

N-(2,6-Diisopropylphenyl)-2-[4-(4-phenylpiperazinyl)butylthio]acetamide dihydrochloride (Compound 19) (m.p.=181.0°–183.0° C.);

N-(2,6-Diisopropylphenyl)-2-[2-(4-benzylpiperazinyl)ethylthio]acetamide dihydrochloride (Compound 20) (m.p.=225.5°–226.5° C.);

N-(2,6-Diisopropylphenyl)-2-[8-(4-phenylpiperazinyl)octylthio]acetamide (Compound 21) (m.p.=76.0°–77.0° C.);

N-(2,6-Diisopropylphenyl)-2-[9-(4-phenylpiperazinyl)nonylthio]acetamide (Compound 22) (m.p.=84.4°–85.6° C.); and N-(2,6-Diisopropylphenyl)-2-[10-(4-phenylpiperazinyl)decylthio]acetamide (Compound 23) (m.p.=72.0°–73.0° C.).

EXAMPLE 2

N-(2,6-Diisopropylphenyl)-2-[12-(4-phenylpiperazinyl)dodecylthio]acetamide (Compound 24)

(1) A mixture of 6.56 g of 1,12-dibromododecane, 3.24 g of N-phenylpiperazine, 2.53 g of triethylamine, and 50 ml of toluene was heated under reflux for 2 hours. To the reaction mixture was added 100 ml of ethyl acetate, and the mixture was washed successively with water and a saturated sodium chloride aqueous solution, and dried over magnesium sulfate. The solvent was evaporated under reduced pressure, and the residue was subjected to column chromatography using a 1:2 mixture of ethyl acetate and hexane as a developing solvent to yield 4.1 g of 1-bromo-12-(4-phenylpiperazinyl)dodecane (m.p.=26.0°–28.0° C.).

(2) To a mixture of 1.47 g of N-(2,6-diisopropylphenyl)-2-(acetylthio)acetamide and 12 ml of methanol was added dropwise 1.7 ml of a 30% aqueous sodium hydroxide solution at 0° C. in an argon atmosphere. After stirring for 30 minutes, a mixture of 2.05 g of 1-bromo-12-(4-phenylpiperazinyl)dodecane synthesized in (1) above and 14 ml of methanol was added thereto, followed by stirring at 60° C. for 1 hour and then at room temperature for 16 hours. To the reaction mixture was added 100 ml of ethyl acetate, and the mixture was washed successively with water and a saturated sodium chloride aqueous solution, and dried over magnesium sulfate. The solvent was evaporated under reduced pressure, and the residue was subjected to column chromatography using a 1:2 mixture of ethyl acetate and hexane as a developing solvent. The resulting crystals were recrystallized from isopropyl alcohol-water to yield 1.66 g of the title compound as white powder (m.p.=76.5°–77.5° C.).

N-(2,6-Diisopropylphenyl)-2-[7-(4-phenylpiperazinyl)heptylthio]acetamide (Compound 25) (m.p.=100.0°–101.4° C.) was obtained in the same manner as in Example 2-(1), except for replacing 1,12-dibromododecane with 1,7-dibromoheptane.

EXAMPLE 3

N-(2,6-Diisopropylphenyl)-2-(4-phenylpiperazinylcarbonylmethylthio)acetamide (Compound 26)

(1) A mixture of 18.8 g of N-(2,6-diisopropylphenyl)-2-chloroacetamide, 8.9 g of ethyl 2-mercaptoacetate, 20.4 g of potassium carbonate, and 100 ml of dimethyl sulfoxide was stirred at room temperature for 1 hour, and a mixture of 25 ml of concentrated hydrochloric acid and 100 ml of water was added thereto. The reaction mixture was extracted with 300 ml of ethyl acetate, and the extract was washed successively with a 1N hydrochloric acid aqueous solution, a sodium hydrogencarbonate aqueous solution, and a saturated sodium chloride aqueous solution, and dried over magnesium sulfate. The solvent was evaporated under reduced pressure to yield 22.6 g of N-(2,6-diisopropylphenyl)-2-(ethoxycarbonylmethylthio)acetamide as white needle crystals (m.p.=124.0°–125.0° C.).

(2) A mixture of 18.0 g of the compound synthesized in (1) above, 4.0 g of sodium hydroxide, 40 ml of water, and 80 ml of ethanol was heated under reflux for 1 hour. To the reaction mixture was added 200 ml of a 1N hydrochloric acid aqueous solution while cooling with ice. The reaction mixture was extracted with 300 ml of ethyl acetate, washed with a saturated sodium chloride aqueous solution, and dried over magnesium sulfate. The solvent was evaporated, and the residue was recrystallized from ethyl acetate to yield 15.8 g of N-(2,6-diisopropylphenyl)-2-(carboxymethylthio)acetamide as white powder (m.p.=168.0°–169.0° C.).

(3) A mixture of 3.09 g of the compound obtained in (2) above, 15 ml of methylene chloride, and 1.5 ml of thionyl chloride was stirred at room temperature for 16 hours, followed by evaporation of the solvent. The residue was dissolved in methylene chloride, and the solution was added dropwise to a mixture of 1.62 g of N-phenylpiperazine, 15 ml of methylene chloride, and 1.7 ml of triethylamine while cooling with ice. After stirring at room temperature for 30 minutes, the solvent was evaporated, and the residue was extracted with 100 ml of ethyl acetate. The extract was washed successively with water, a sodium hydrogencarbonate aqueous solution, and a saturated sodium chloride aqueous solution, and dried over magnesium sulfate. The solvent was evaporated under reduced pressure, and the residue was purified by column chromatography using, as a developing solution, a mixture of ethyl acetate and hexane at a ratio varied from 1:2 to 1:0. Crystallization from ethanol afforded 2.04 g of the title compound as white needle crystals (m.p.=152.5°-153.0° C.).

N-(2,6-Diisopropylphenyl)-2-(4-benzylpiperazinylcarbonylmethylthio)acetamide monohydrochloride (Compound 27) (m.p.=198.0°-199.0° C.) was obtained in the same manner as in Example 3-(3), except for replacing N-phenylpiperazine with N-benzylpiperazine.

EXAMPLE 4

N-(2,6-Diisopropylphenyl)-2-[2-(4-phenylpiperazinyl)ethylsulfonyl]acetamide (Compound 28)

(1) A solution of 17.6 g of m-chloroperbenzoic acid in 40 ml of methylene chloride was added dropwise to a solution of 10.6 g of N-(2,6-diisopropylphenyl)-2-(2-chloroethylthio)acetamide, prepared in the same manner as in Example 1-(1), in 300 ml of methylene chloride under cooling with ice, followed by stirring at room temperature for 16 hours. The insoluble matter was collected by filtration, washed successively with a saturated sodium hydrogencarbonate aqueous solution, sodium thiosulfate, a saturated sodium hydrogencarbonate aqueous solution, and a saturated sodium chloride aqueous solution, and dried over anhydrous magnesium sulfate. The solvent was evaporated under reduced pressure, and the residue was crystallized from diisopropyl ether-ethyl acetate to obtain 8.0 g of N-(2,6-diisopropylphenyl)-2-(2-chloroethylsulfonyl)acetamide (m.p.=166.0°-168.0° C.).

(2) A mixture of 3.46 g of N-(2,6-diisopropylphenyl)-2(2-chloroethylsulfonyl)acetamide synthesized in (1) above, 1.62 g of N-phenylpiperazine, and 50 ml of toluene was heated under reflux for 4 hours. To the reaction mixture was added 100 ml of ethyl acetate, and the mixture was washed successively with a sodium hydrogencarbonate aqueous solution and a saturated sodium chloride aqueous solution, and dried over magnesium sulfate. The solvent was evaporated under reduced pressure, and the residue was subjected to column chromatography using a mixture of ethyl acetate and hexane at a ratio varying from 1:1 to 1:0 as a developing solvent. The solvent was evaporated, and the residue was dissolved in ethyl acetate and crystallized from a 4N hydrochloric acid solution in ethyl acetate to obtain 3.33 g of the title compound as white powder (m.p.=197.0°-200.0° C.).

INDUSTRIAL APPLICABILITY

Having a potent ACAT inhibitory activity, the compound of the present invention provides an excellent agent for atherosclerosis inhibition or for cholesterol reduction.

TEST EXAMPLE 1

Test of ACAT Inhibitory Activity

The test was carried out in accordance with the method described in *J. Lipid Res.*, Vol. 22, p. 271 (1981).

A microsome fraction of a rabbit small intestine prepared in a usual manner was suspended in a 0.04N potassium phosphate buffer solution (pH 7.4) containing 0.1N sucrose, 0.03N ethylenediaminetetraacetic acid (EDTA), and 0.05N potassium chloride. Each drug to be tested was dissolved in dimethyl sulfoxide.

The rabbit small intestinal microsome fraction suspension prepared above (250 μg as protein) and [1-$^{14}$C]oleyl coenzyme were added to a 0.05N phosphate buffer solution (pH 7.4) containing 1% bovine serum albumin, followed by addition of a drug to be tested in a varied concentration. The total volume of the mixture was adjusted to 500 μl to prepare a sample. For control, a sample was prepared in the same manner, except for adding no test drug. The sample was incubated at 37° C. for 6 minutes, and the reaction was terminated by addition of a mixture of chloroform and methanol (mixing ratio=2:1). After stirring, the chloroform layer was collected and concentrated to dryness. A 30 μl portion of a cholesterol oleate solution in chloroform (concentration: 10 mg/ml) was added to the residue, and the mixture was spotted on a silica gel thin layer plate (Kieser Gel 60F$_{254}$ Art 5715, manufactured by Merck & Co., Inc.) and developed with a mixture of hexane and ethyl acetate (mixing ratio=100:3). A gel portion corresponding to cholesterol oleate was scraped, and its radioactivity was measured with a liquid scintillation counter (LSC-3000, manufactured by Aloka Co., Ltd.). Percent inhibition on ACAT activity was calculated using the following equation to obtain an IC$_{50}$ value.

Percent inhibition on *ACAT* activity (%) =

$$\frac{(ACAT\ \text{activity of control}) - (ACAT\ \text{activity of test sample})}{(ACAT\ \text{activity of control})} \times 100$$

The results obtained are shown in Table 1 below.

TABLE 1

| Test Drug | IC$_{50}$ | Test Drug | IC$_{50}$ |
|---|---|---|---|
| Compound 1 | ++ | Compound 14 | ++ |
| Compound 2 | ++ | Compound 15 | ++ |
| Compound 3 | ++ | Compound 16 | ++ |
| Compound 4 | ++ | Compound 17 | ++ |
| Compound 5 | ++ | Compound 18 | ++ |
| Compound 6 | ++ | Compound 19 | ++ |
| Compound 7 | ++ | Compound 21 | +++ |
| Compound 8 | ++ | Compound 22 | ++ |
| Compound 9 | ++ | Compound 23 | ++ |
| Compound 10 | ++ | Compound 24 | ++ |
| Compound 11 | ++ | Compound 25 | ++ |
| Compound 12 | ++ | Compound A | + |

Note:
Symbols in Table 1 each indicate strength of the activity as follows:
+: 1000 - 100 nM
++: 100 - 10 nM
***: 10 - 1 nM
Compound A: N-(2,4-Difluorophenyl)-N-[(4-neopentylphenyl)methyl]-N-heptylurea (the compound described in JP-A-60-41655)

TEST EXAMPLE 2

Test of Lipid Reduction in Normal Rat

Five 5-week-old male Wister rats per group were used as test animals. Each test drug was orally administered to the rat at a dose of 100 mg/kg for 3 days. A blood sample was taken from the rat having been deprive of food for 18 hours from the final administration, and the serum was separated. A total cholesterol value and a total triglyceride value were measured with an autoanalyzer (Hitachi 7150) in accordance with an enzyme method (Autosera, manufactured by Daiichi Kagaku K.K.). Lipoprotein was separated by a precipitation method (HDL-C.2, manufactured by Daiichi Kagaku K.K.), and the cholesterol in the lipoprotein was determined by an enzyme method. Five ml/kg of each test drug suspended in a 0.2% aqueous solution of sodium carboxymethyl cellulose was administered. For control, the same sodium carboxymethyl cellulose solution containing no test drug was administered. The results obtained are shown in Tables 2 and 3 below.

TABLE 2

| Test Drug | Total Cholesterol in Serum | | Total Triglyceride in Serum | |
|---|---|---|---|---|
| | Measured Value (mg/dl) | Percent Change* (%) | Measured Value (mg/dl) | Percent Change* (%) |
| Control | 59.0 ± 3.0 | — | 88.4 ± 6.6 | — |
| Compound 1 | 51.8 ± 3.2 | −12.2 | 51.6 ± 2.7 | −41.6 |
| Compound B | 63.2 ± 3.1 | 7.1 | 108.0 ± 5.1 | 18.8 |

TABLE 3

| Test Drug | Cholesterol in High Density Lipoprotein | | Cholesterol in Low Density Lipoprotein | |
|---|---|---|---|---|
| | Measured Value (mg/dl) | Percent Change* (%) | Measured Value (mg/dl) | Percent Change* (%) |
| Control | 44.5 ± 0.9 | — | 11.8 ± 1.1 | — |
| Compound 1 | 46.0 ± 1.7 | 3.4 | 5.8 ± 2.0 | −50.8 |
| Compound B | 51.4 ± 2.2 | 15.5 | 11.8 ± 5.1 | 0.0 |

Note: "Percent change" in Tables 2 and 3 is a rate of change in the respective cholesterol value compared with the control.

Compound B: N-(2,4,6-Trimethoxyphenyl)-2,2-dimethyldodecylamide (the compound described in JP-A-63-253060).

The results in Table 3 prove that Compound 1 according to the present invention specifically reduces low density lipoprotein which accelerates arteriosclerosis and is therefore excellent as a lipid reducing agent.

What is claimed is:

1. An anilide compound represented by formula (I):

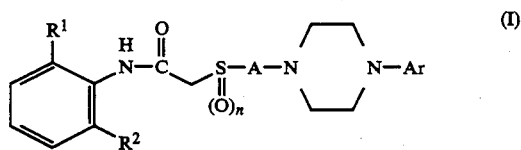

wherein $R^1$ and $R^2$, which may be the same or different, each represent an alkyl group having 1 to 4 carbon atoms;

n represents 0, 1 or 2;

A represents an alkylene group having 1 to 14 carbon atoms or a group represented by —$CH_2CO$—; and Ar represents:
- a phenyl group,
- a phenyl group substituted with a halogen atom, a nitro group, an alkyl group having 1 to 4 carbon atoms, an alkoxy group having 1 to 4 carbon atoms, an alkanoyl group having 2 to 5 carbon atoms or a trifluoromethyl group,
- a benzyl group,
- a pyridyl group,
- a pyridyl group substituted with a halogen atom or a trifluoromethyl group,
- or a pyrimidyl group,
- or a pharmaceutically acceptable salt thereof.

2. An anilide compound or a pharmaceutically acceptable salt thereof as claimed in claim 1, wherein $R^1$ and $R^2$ are each an isopropyl group; n is 0; A is an alkylene group having 1 to 14 carbon atoms; and Ar is a phenyl group.

3. An anilide compound or a pharmaceutically acceptable salt thereof as claimed in claim 1, wherein $R^1$ and $R^2$ are each an isopropyl group; n is 0; A is an alkylene group having 6 or 8 carbon atoms; and Ar is a phenyl group.

4. An anilide compound or a pharmaceutically acceptable salt thereof as claimed in claim 1, wherein $R^1$ and $R^2$ are each an isopropyl group; n is 0; A is an alkylene group having 6 carbon atoms; and Ar is a phenyl group.

* * * * *